United States Patent
Bao et al.

(10) Patent No.: US 10,301,341 B2
(45) Date of Patent: May 28, 2019

(54) TECHNOLOGY FOR EXTRACTING AND PREPARING HIGH-PURITY RAFFINOSE FROM DEFATTED WHEAT GERM

(71) Applicant: ZHEJIANG UNIVERSITY, Hangzhou, Zhejiang Province (CN)

(72) Inventors: Zongbi Bao, Hangzhou (CN); Minhui Huang, Hangzhou (CN); Shuran Duan, Hangzhou (CN); Qianqian Zhou, Hangzhou (CN); Zhiguo Zhang, Hangzhou (CN); Qiwei Yang, Hangzhou (CN); Baogen Su, Hangzhou (CN); Huabin Xing, Hangzhou (CN); Qilong Ren, Hangzhou (CN); Yiwen Yang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/550,747

(22) PCT Filed: May 7, 2015

(86) PCT No.: PCT/CN2015/078440
§ 371 (c)(1),
(2) Date: Aug. 11, 2017

(87) PCT Pub. No.: WO2016/161686
PCT Pub. Date: Oct. 13, 2016

(65) Prior Publication Data
US 2018/0051047 A1 Feb. 22, 2018

(30) Foreign Application Priority Data
Apr. 9, 2015 (CN) .......................... 2015 1 0164653

(51) Int. Cl.
| | | |
|---|---|---|
| *C07H 1/08* | (2006.01) |
| *C07H 3/06* | (2006.01) |
| *C13K 13/00* | (2006.01) |
| *A23L 5/20* | (2016.01) |
| *A23L 5/30* | (2016.01) |
| *B01D 15/18* | (2006.01) |
| *B01D 61/44* | (2006.01) |
| *B01D 71/08* | (2006.01) |

(52) U.S. Cl.
CPC ................. *C07H 1/08* (2013.01); *A23L 5/23* (2016.08); *A23L 5/30* (2016.08); *B01D 15/1821* (2013.01); *B01D 61/44* (2013.01); *B01D 71/08* (2013.01); *C07H 3/06* (2013.01); *C13K 13/00* (2013.01); *A23V 2002/00* (2013.01); *A23V 2250/622* (2013.01); *B01D 2311/04* (2013.01); *B01D 2311/26* (2013.01); *Y02A 20/134* (2018.01)

(58) Field of Classification Search
CPC .. C07H 1/08; C07H 3/06; C13K 13/00; A23L 5/23; A23L 5/30; B01D 61/44; B01D 71/08; B01D 15/1821; A23V 2250/622; A23V 2002/00
USPC ............................ 127/46.2, 53, 48
See application file for complete search history.

(56) References Cited

U.S. PATENT DOCUMENTS

| | | | | |
|---|---|---|---|---|
| 3,718,560 A | * | 2/1973 | Sugiyama et al. ..... | B01D 61/44 127/46.1 |
| 2004/0006222 A1 | * | 1/2004 | Paananen ............. | B01D 61/022 536/123.13 |

FOREIGN PATENT DOCUMENTS

| | | | |
|---|---|---|---|
| CN | 101367846 | * | 2/2009 |
| CN | 101372498 A | | 2/2009 |
| CN | 102408400 | * | 4/2012 |
| CN | 102408400 A | | 4/2012 |
| CN | 103113422 A | | 5/2013 |

OTHER PUBLICATIONS

Canella et al. Extraction of Gossypol and Oligosaccharides From Oilseed Meals. Journal of Food Science—vol. 42, No. 5, p. 1218-1219 (1977). (Year: 1977).*

* cited by examiner

*Primary Examiner* — Yih-Horng Shiao
(74) *Attorney, Agent, or Firm* — Jiwen Chen

(57) ABSTRACT

The present invention discloses a process for preparing high-purity raffinose from defatted wheat germ comprising the steps of percolate extraction of raffinose from defatted wheat germ, decoloration by extraction from the abstraction liquid, electrodialysis desalination, impurity removal by simulated moving bed, concentration and crystallization, with the absolute purity of raffinose as high as 98% and the recovery up to 75%. The process is not only reliable and easy to operate, but also easy to realize industrial production and control the parameters.

5 Claims, 2 Drawing Sheets

TECHNOLOGY FOR EXTRACTING AND PREPARING HIGH-PURITY RAFFINOSE FROM DEFATTED WHEAT GERM

This is a U.S. national stage application of PCT Application No. PCT/CN2015/078440 under 35 U.S.C. 371, filed May 7, 2015 in Chinese, claiming priority of Chinese Application No. 201510164653.8, filed Apr. 9, 2015, all of which are hereby incorporated by reference.

TECHNICAL FIELD

The present invention is related to the chemical engineering technology field, more specifically, a process for preparing high-purity raffinose from defatted wheat germ. More specifically, percolate extracting, decoloring by extracting, electrodialysis desalinating, removing impurity by simulated moving bed, concentrating and crystallizing are used. High-purity raffinose can be obtained by extracting and separating from defatted wheat germ.

BACKGROUND OF THE INVENTION

As a functional oligosaccharide, raffinose is widely existed a variety of natural products, and standard naming is beta-D-fructofuranosyl D-galactopyranosyl-(1→6)-D-glucopyranoside. It is non-reduced sugar, composed by galactose, glucose and fructose, with the following structure form:

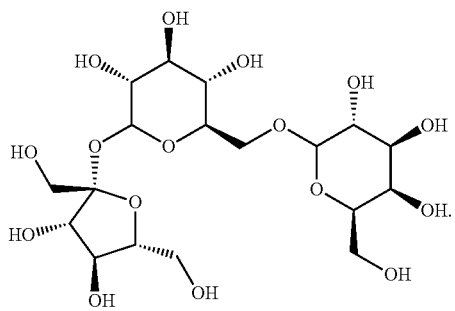 [SMILES: OC[C@H]1OC(OC[C@H]2OC(O[C@]3(CO)O[C@H](CO)[C@@H](O)[C@@H]3O)[C@H](O)[C@@H](O)[C@@H]2O)[C@H](O)[C@@H](O)[C@H]1O]

Raffinose was deemed anti-nutritional factors on the grounds that lack of α-galactosidase in humans. Raffinose cannot be decomposed and absorbed in the small intestine, so it is accumulated in large intestine and used by intestinal flora. After passing through to the large intestine, raffinose is utilized by bifidobacteria, improving the propagation of bifidobacterium and producing short-chain fatty acid. So it can bring down the intestinal pH, increase humidity of faeces, and withhold harmful bacterium's multiplication. So it can be added to food ingredients as prebiotics. Raffinose also has certain protective effect on liver injury. It reduces formation of toxic metabolites by withholding harmful bacterium's multiplication, and then reduce hepatic detoxifying burden. Meanwhile, it has many physiological functions including anticancer, anti-inflammatory, decrease of serum cholesterol and immuno-enhancement. High-purity raffinose can be used as sweeteners in diet food with low-calorie. And it also can be used in the series foods for diabetics. In addition, as a nonionic surfactant, raffinose fatty glyceride, synthesizing with raffinose, has many features including high-security, minor irritant to the skin and low-allergia, therefore it can also be applied in cosmetic especially. With the characteristic above, raffinose is extensive in the fields of food, health products, medicine, daily chemical industry.

Raffinose is widely existed a variety of natural products, such as cottonseed, beets, leguminous plants, wheat and so on. With a high raffinose content in cottonseed and wheat germ, the content of cottonseed is about 4%~9%, with the exact same as defatted wheat germ. Defatted wheat germ is the by-product after extraction of wheat germ oil. Underlying amount of wheat germ is up to 2,000~2,500,000 tons every year in our country. As "the nutrition treasure house of human nature", it has most abundant and high-quality protein, fatty, vitamins and minerals. People have been interested in its high nutritive, and constantly develop serial functional foods. The deep processing technology of wheat germ products is just starting out. Preparing high-purity raffinose from defatted wheat germ is significant in the acceleration of comprehensive utilizing wheat germ.

In present technology, the process for preparing high-purity raffinose from defatted wheat germ is that defatted wheat germ was immersed and extracted by high concentration alcohol-containing liquid to obtain raffinose, followed by decolorization, purification and refining of extracting solution. Wei Peipei (Wei Peipei, extraction and preparation of raffinose from defatted wheat germ, 2011, Jiangnan University, Wuxi) reported on a process for preparing high-purity raffinose from defatted wheat germ. Firstly, an extract is obtained by agitation leaching process from wheat germ, with agitation leaching for 2.5 hours by 75% aqueous alcohol at 50° C., with ratio of solid to liquid of 1:13. And the extracts rate of raffinose is 83.65%. Decoloration is operated in the system containing alcohols, with the best decolour conditions are pH 5.0, activated carbon concentration 4% (w/v), decoloring temperature 50° C., decoloring time 2 hours. Preliminary separating of raffinose by crystallization with the decolored solution, and raffinose can obtained by recrystallization.

The above process, the optimum total yield is 28.9% (raffinose content of defatted wheat germ is 7.95%), and the yield is not high. There are some problems with commercial scale, For example, large quantity of solvent in static method, low extraction ratio, long periods, extracting for several times and high requirement of equipment. High activated carbon consumption is used in the decoloring process, and hardly utilized repeatedly of activated carbon powder. The purity increase of raffinose is not ideal, the purity of raffinose is up to 98% after crystallization process for several times, which led to low recovery of raffinose. With the increase of crystallization time, industrial-scale and efficiency is limited.

Therefore, it still has some disadvantages in the prior art process for preparing high-purity raffinose from defatted wheat germ, not suitable for industrial-scale production, some improvement should do in the aspect of cost control, yield. Thus, process should be simplified and optimized based on technology that already exists, to seek a preparing method with simple process, low cost and high yield.

SUMMARY OF THE INVENTION

The present invention provides a method of preparing high-purity raffinose from defatted wheat germ, with the absolute purity of raffinose up to 98% and the recovery as high as 75%. The process is simple and reliable, easy-to-handle, parameter controlling.

A method of preparing high-purity raffinose from defatted wheat germ comprises the steps of:

(1) Percolation extraction: Percolation extracting the defatted wheat germ, and collecting percolate containing raffinose, the process comprises the steps of:
loading the percolation column with defatted wheat germ, then adding volume concentration 60%~90% aqueous alcohol, percolating 20~60 minutes at 40~80° C. Percolating at constant pressure with adding extraction solvent continuously with flow velocity at 0.5~3 times the number of the volume of defatted wheat germ every hour. Collecting extraction containing raffinose at the exit, until the volume of extraction 3~5 times the number of the volume of the defatted wheat germ.

The preferred volume of extraction solvent is 60~100 percent of the volume of defatted wheat germ.

Extraction of Step (1) is operated with 60%~90% aqueous alcohol at 40~80° C., for large solubility of raffinose at this concentration and small solubility of other ingredients in defatted wheat germ, to improve raffinose extraction yield and the purity of raffinose with higher extract rate and little harmful elements. The absolute purity of raffinose is up to 98% and mass percent of raffinose is 15%~25% (on dry base). The extract also contains some impurities, such as pigment, salt, monosaccharide, sucrose as so on. The optimum is 60° C., 80% aqueous alcohol. The defatted wheat germ is immersed for 30~60 minutes, and full swelled defatted wheat germ, to guarantee the defatted wheat germ immersing in extraction solvent totally. Adding extraction solvent continuously while collecting percolate is to decrease the consumption of solvent and reduce energy consumption of recovered solvents. The preferred flow velocity is 0.5~3 times the number of the volume of defatted wheat germ every hour. So it not only ensures plenty of contact hours to mix extraction solvent and the defatted wheat germ to improve utilization rate of solvent, but also covers production capacity.

Diacolation column is single-column or columns in series. In the operation of columns in series, the weakly alcoholic solutions, recovered with deionized water after percolating at an anterior column, can be used as a swelling solvent at a posterior column, to avoid recovery of distilling solvent and lower energy consumption.

To improve the utilization efficiency of the solvent, the solvent can be recycled in the following way: adding deionized water from the top down, controlling flow velocity 0.5~1.5 times the number of the volume of defatted wheat germ, and collecting mixed fluid of extraction solvent and water, and then recovering solvent by distilling.

(2) Extracting decoloration: concentrating percolate of Step (1) to remove alcohol and obtain a solid product. Dissolving solid substance followed by filtering to insoluble substance. Extracting the filtrate with organic solvent and concentrating the aqueous phase, obtaining the destaining solution.

The preferred volume of solution with dissolving solid substance of Step (2) is 15%~35% of the percolate volume. If volume is overlarge after removing alcohol, ethanol is not removed completely, which will influence the extracting efficiency. So concentration progress should be controlled to ensure complete removal. The recycled ethanol can be used as an extractant of percolation.

The preferred organic solvent is n-butanol, iso-butanol, ethyl acetate, n-hexane and petroleum ether. The volume is 0.5~1.5 times the number of filtrate volume.

The more preferred organic solvent is n-butanol, the volume is 0.5~1.5 times the filtrated volume, most pigment can be removed, so the aqueous phase from become canary yellow from sandy.

An organic solvent can be recycled by rotary evaporating after extraction, and cycled as an extractant. The aqueous phase can be obtained after 30~120 mins' standing after extraction of this step. In comparison to decoloration using activated carbon fixed bed, this operation has merits of simpler equipment and operation, lower costs, and well decolorization effect.

(3) Desalination: Handling the destaining solution of Step (2) with a microporous membrane of the drainage, diluting the solution with water to get pretreatment liquid with 50~150 mg/mL solid concentration, and desalinating the pretreatment liquid with selectroosmosis for 2~3 hours.

The aperture of the microporous membrane of the drainage is 0.45 μm.

The electrodialysis desalination process comprises the steps of: taking the pretreatment liquid and pure water as a concentrated phase and a dilute phase, respectively, and taking $Na_2SO_4$ as polar water. The pretreatment liquid, pure water and polar water were cycled in the instrument. Desalinating for 2~3 hours under constant voltage and velocity.

The preferred mass concentration of $Na_2SO_4$ is 3%~8% and the volume ratio of the polar water, pretreatment liquid and pure water is 0.25:1: (1~3). The concentration of polar water should not be too high, it will bring equipment corrosion to electrodialysis apparatus.

The preferred desalination conditions: operating voltage is 15~30 V and the liquid flow rate is 10~30 L/h.

Higher voltage, more thorough of desalination and larger energy consumption.

Compared to other desalination methods, electroosmosis has merits of operational continuity, no increase of other impurity, no-environmental pollution, low cost, lower sugar losses. Salt and a small amount of pigment can be removed, so it can avoid the effect of salt to subsequent separation and the effect on the yield in crystallization, and enhance separation efficiency and total yield of raffinose.

(4) SMB (simulated moving bed) adsorption: separating the pretreatment liquid of Step (3) with electrodialysis, and collecting the flow containing raffinose. The supersaturated syrup was obtained by concentrating.

The simulated moving bed equipment has conventional four areas. Synthesizes device capability and equipment costs, there are 2~4 chromatogram columns in each area, with inputting and outputting continuously. The device has two inlets, i.e. feed inlet and elution inlet, respectively. And it also has two outlets, i.e. extraction exit and residue exit.

The four ports simulated moving bed was dived into four regions by exits and inlets: I region: between elution inlet and extraction exit, the major functions were to elute the impurities containing sucrose, and regenerate stationary phase. II region: between extraction exit and feed inlet, the major functions are to enrich the impurities containing sucrose. III region: between feed inlet and residue exit, the major function is to obtain high-purity raffinose from raffinate. IV region: between residue exit and extraction exit, this is parse area (The structure is shown in FIG. 3).

The fixed-bed adsorber of chromatographic column is extreme acidic (Ca) ion exchange resin and (Na) ion exchange resin, with water as an eluent.

Further, the crosslinking degree of adsorbent is 2%~8% and the size is 100~400 mesh.

By affinity difference between adsorbents for metal ions and all sorts of sugars and polyols, or relative difference between pore size of resin and size of sugar alcohols, raffinose and other sugars will be separated completely. The extreme acidic (Ca) ion exchange resin and (Na) ion exchange resin are handled with hydrogen ion exchange resin according to national standards GB/T 5476-1996. The resin is cleaned with hot water to no bubble. Then the glass chromatographic column is packed by wet method. After acid washing and alkali washing, it is transferred by the corresponding ion salt solution with solution of 1M, and the volume of the fixed bed is 3~5 times. Flow velocity is controlled at 0.5 times bed every hour, and then it is washed by deionized water. The deionized water is used as an eluent, to avoid introducing organic solvent, such as acetonitrile.

The preferred mesh is 200~400 meshes, the preferred resin is extreme acidic (Ca) ion exchange resin with 2% crosslinking degree. The lower the resin crosslinking degree, the greater the porosity, the faster the exchange rate of ion. The more finely the resin particle size, the faster mass transfer, the lower HETP, the higher column efficiency, the higher separation efficiency.

The preferred separate operation of the simulated moving bed equipment: the switching time is 30~90 s, velocities of flow in area I, area II, area III and area IV are 0.67~0.86, 0.44~0.70, 0.47~0.79 and 0.41~0.60, respectively.

The preferred switching time is 30~90 s, lower switching time contributes to improvement of separation efficiency. But the switching time of rotary valves is less. The wear of rotary valves is higher, which will affect the service life. So 30~90 s is the optimum.

The non-dimensional flow rate is defined as $$m_j = \frac{Q_j^{TMB} t_s - V\varepsilon}{V(1-\varepsilon)},$$

$Q_j^{TMB}$ is velocity in each area, V is volume of single chromatographic column, $\varepsilon$ is the total porosity of single chromatographic column, $t_s$ is the switching time, $m_j$ is the flow rate in each area.

The optimum is 0.75 in area I, 0.47 in area II, 0.51 in area III and 0.5 in area IV.

The isothermal operation is used in the simulated moving bed equipment and the preferred column temperature is 60~80° C. The temperature works both ways in separating effect. With the increase of temperature, mass transfer efficiency increases and the column efficiency improves. But the separation selectivity is smaller and separating effect is worse at the same time. The purity of raffinose is almost 95% in 60~80° C. comprehensively considered, the preferred separation temperature is 60° C.-80° C., and the more preferred column temperature is 60~65° C., with the best effect, low-solvent consumption and superior productivity of stationary phase.

Desalination liquid can be separated in two flows, one is the raffinate containing raffinose (the purity of raffinose 90%~95%, always>93%), the other is extract containing other sugar, such as sucrose (the purity of raffinose<25%). The raffinate is concentrated as supersaturated syrup.

(5) Crystallizing the supersaturated syrup and obtaining the white crystallization L-arabinose after drying.

The process of the crystallization comprises the steps of:

The supersaturated syrup of Step (4) was dissolved in alcohol at 60~90° C., and then reducing the temperature to 25~40° C. Inducing crystallization by adding some raffinose, filtering after crystallizing of 12~36 hours. Then obtaining the pure raffinose with purity up to 98% after drying in a vacuum oven at 30~50° C. The crystallization mother liquor was incorporated into the electrodialysis desalination fluid and separated by simulated moving bed, to improve the recovery rate of raffinose.

The preferred alcohol is methanol or ethanol, the ratio of volume and the supersaturated syrup is (3~6) L: 1 kg.

The preferred falling temperature rate is 0.5~3° C./min, crystallization temperature range is -5~20° C.

Term's meaning in the present invention is shown as followed:

The solution with solid content of 100 mg/mL means that there are 100 mg solid in the solution after being concentrating to constant quality. Due to complex composition, there are some insoluble substances. And the total mass is the whole quality of system, including the quality of suspension or precipitation.

Dry basis is solid mass after drying solution, which means the total mass of all solvents in solution.

The process of the present invention is based on simulated moving bed separation as the core technology to remove other sugar from raffinose extract, such as monosaccharide and sucrose. Desalination is performed by electroosmosis, to reduce impacts of salt on crystallization, to obtain the higher extraction yield of raffinose on the condition of simple technics and low-cost.

The process of the present invention uses percolation to extract raffinose from defatted wheat germ. Compared with the conventional solvent leaching method, it maintains the highest temperature gradients out of and into the cells. It can also accelerate the dissolved mass transfer, to improve the extraction rate prominently and reduce solvent consumption. The raffinose extraction yield is more than 95%. Mass percent of raffinose in diacolation extract is between 15%~25% (on dry basis).

The process of the present invention uses extraction to remove pigment from diacolation extract. It has one trait that it has the greater extraction ability of organic solvent to pigment than raffinose. So it can extract pigment selectively, and it has discoloration effect. In comparison to decoloration using activated carbon fixed bed, this operation has the merits of simpler equipment and operation, lower costs. And electrodialysis is used as low-cost desalination, to remove salt and a small amount of pigment in destaining solution, which contribute to subsequent separation and purification process with synergy of each step.

The process of the present invention uses simulated moving bed to separate sucrose and raffinose. With adsorption separation performance of raffinose and other sugars, raffinose and other sugars will be separated completely. Water is used as an eluent without any pollution. It is a fully automated process, has the advantages of high efficient, small floor occupation and lower production costs.

Primary crystallization is used to raffinose with the purity up 98%, to reduce the raffinose loss of recrystallization for several times, to improve the yield of raffinose.

In general, the present invention combines the above five steps together to prepare high-purity raffinose from defatted wheat germ. Compared with the prior art, it has the active effects as followed:

The process route of the present invention is simply, the demand for production equipment is low, operation is simple. The solvent can be recycled, so most of the products in the process can be recycled. The yield of raffinose greatly increases by using simulated moving bed. The process route has such advantages as simple process, low cost, high yield with industrial mass production.

DETAILED DESCRIPTION OF THE INVENTION

Figure 1:
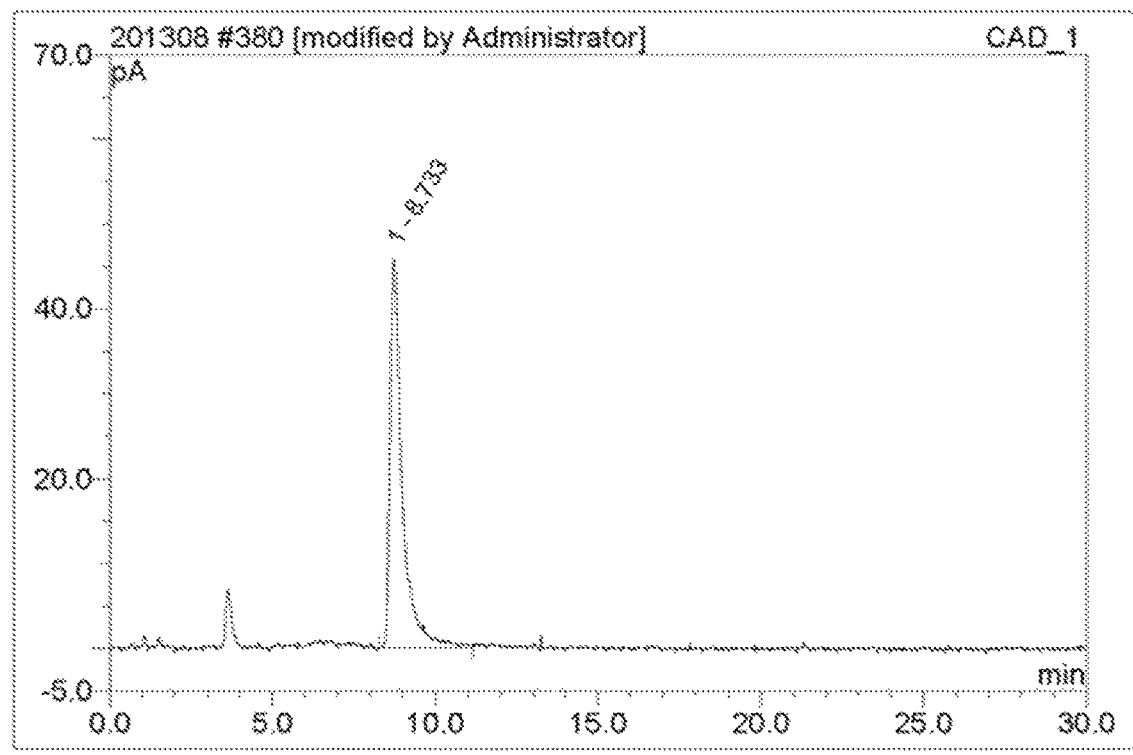
FIG. 1 HPLC chromatogram of product raffinose of the present invention

The present invention is described in reference to the following specific embodiments, basing on the preparation methods and test results of high-purity raffinose.

Embodiment 1

(1) 200 g defatted wheat germ (wherein raffinose is 4.6% by mass) was packed in diacolation column (Φ 4.0×50 cm) by wet method. The accumulation volume is about 500 mL after loading evenly. The defatted wheat germ is immersed for 30 min and under constant temperature of 60° C., and full swelling of defatted wheat germ.

The 80% aqueous ethanol was added from top of adsorption column continuously after opening the outlet valve of diacolation column. The flow rate was controlled at 18~20 mL/min, until the collected percolate volume of 1371 mL.

230 g defatted wheat germ was packed in diacolation column by the wet method. The accumulation volume is about 592 mL. Other conditions are as above with the collected percolate volume of 1948 mL.

150 g defatted wheat germ was packed in diacolation column by the wet method. The accumulation volume is about 355 mL. Other conditions are as above with the collected percolate volume of 1066 mL.

The percolates were combined, and used as a raw material liquid for subsequent operations. The solids concentration is 28.6 mg/mL after analysis, with purity of raffinose as 20.8% and the yield as 97.8%. (26 g raffinose)

(2) The 500 mL percolate was concentrated to thick status, and then added deionized water, to ensure that the total volume is less than 150 mL. The filtrate was diluted to 150 mL after filtered by cloth and membrane successively. 135 mL solution is extracted by equal numbers of n-butanol. With analysis of aqueous phase after extraction, the purity of raffinose is 28.9%, the solid concentration is 98.6 mg/mL, and the recovery of raffinose is 92%.

Aqueous phase was concentrated to remove alcohol. The solid concentration of 100 mg/mL is prepared by adding deionized water.

(3) Desalination: the decoloring solution was handled with 0.45 μm microporous membrane of the drainage before adding electrodialysis with 5 wt % $Na_2SO_4$ as polar water. The electrodialysis conditions: voltage is 25 V, the flow of material was 20 L/h. The preferred volume ratio of polar water, the liquor, and pure water is 0.25:1:1. The electrical conductivity of desalting chamber was decreased from 979 μS/cm to 85.7 μS/cm after desalination for 2 hours. 481 mL liquor was collected containing 19.51 g arabinose, with purity up to 60%. And desalination rate was as high as 91% and the recovery of this step was 95%.

(4) SMB (simulated moving bed) adsorption: simulated moving bed equipment is composed of eight stainless (25 cm*0.46 cm) steel columns in series with packing with extreme (Na) ion exchange resin of 200~400 mesh, 2% crosslinking degree. The desalted solution was added in simulated moving bed equipment from feed inlet with flow rate of 0.1 mL/min. The flow rate in every area is 0.75 in area I, 0.47 in area II, 0.51 in area III and 0.5 in area IV. The switching time is 60 seconds, and the separation temperature is 60° C. The raffinate containing raffinose was obtained from residue exit. After analysis by HPLC, the purity of raffinose is 93%, the solid concentration is 98.6 mg/mL, and the recovery of raffinose is 93%.

(5) Crystallization: the effluent was distillated reduced pressure to syrup before adding 85% ethanol solution, and with solid to liquid ratio was 1:6. The solution was refluxed for 20 minutes in a water bath of 90° C., and then cooled down to room temperature with adding a small amount of raffinose. The solution stayed in the refrigerator of 5° C. for 24 hours. The crystal was filtered and washed with little absolute ethanol. The product was dried in a vacuum oven at 30° C. for 6 hours. 2.02 g raffinose can be gotten with purity as 98.5%. The recovery of raffinose in whole process was 68% basing on the mass of raffinose in defatted wheat germ.

Mother liquor after crystallization could be cycled in the step of adsorption separation, so recovery was improved to 79.5% basing on recovery of crystallization as 100%.

Embodiment 2

The 500 mL extract of Step (1) was handled as the same operation of Step (2). The purity of raffinose is 28.7%, the solid concentration is 100.7 mg/mL.

(3) 5 wt % $Na_2SO_4$ was used as polar water. The electrodialysis conditions: voltage is 25 V, the flow of material was 15 L/h. The electrical conductivity of desalting chamber was decreased from 992 μS/cm to 108 μS/cm after desalination for 2.5 hours.

(4) SMB (simulated moving bed) adsorption: simulated moving bed equipment is composed of eight stainless steel columns (25 cm*0.46 cm) in series with packing with extreme (Na) ion exchange resin of 200~400 mesh, 4% crosslinking degree. The desalted solution was added in simulated moving bed equipment from feed inlet with flow rate of 0.1 mL/min. The flow rate in every area is 0.75 in area I, 0.47 in area II, 0.51 in area III and 0.5 in area IV. The switching time is 60 seconds, and the separation temperature is 60° C. The raffinate containing raffinose was obtained from residue exit. After analysis by HPLC, the purity of raffinose is 92%, and the recovery of raffinose is 91%.

(5) Crystallization is added 85% ethanol solution for 12 hours, with solid to liquid ratio was 1:8. 1.94 g raffinose can be gotten with purity as 98.5%. The recovery of raffinose in whole process was 65.4% basing on the mass of raffinose in defatted wheat germ. Mother liquor after crystallization could be cycled in the step of adsorption separation, so recovery was improved to 76.1% basing on recovery of crystallization as 100%.

Embodiment 3

The operation of Step (1) and Step (2) is the same as Embodiment 1.

(3) 5 wt % $Na_2SO_4$ was used as polar water. The electrodialysis conditions: voltage is 25 V, the flow of material was 15 L/h. The electrical conductivity of desalting chamber was decreased from 1017 μS/cm to 115 μS/cm after desalination for 2.5 hours.

(4) SMB (simulated moving bed) adsorption: simulated moving bed equipment is composed of eight stainless steel columns (25 cm*0.46 cm) in series with packing with extreme (Ca) ion exchange resin of 200~400 mesh, 2% crosslinking degree. The desalted solution was added in simulated moving bed equipment from feed inlet with flow rate of 0.1 mL/min. The flow rate in every area is 0.75 in area I, 0.47 in area II, 0.51 in area III and 0.5 in area IV. The switching time is 60 s, and the separation temperature is 65° C. The raffinate containing raffinose was obtained from residue exit. After analysis by HPLC, the purity of raffinose is 91%, and the recovery of raffinose is 92%.

(5) Crystallization is added 80% methanol solution for 24 hours, with solid to liquid ratio was 1:8. 1.92 g raffinose can be gotten with purity as 98.2%. The recovery of raffinose in whole process was 64.7% basing on the mass of raffinose in defatted wheat germ. Mother liquor after crystallization could be cycled in the step of adsorption separation, so recovery was improved to 77% basing on recovery of crystallization as 100%.

Embodiment 4

The operation of Step (1), Step (2), Step (3) and Step (4) is the same as Embodiment 3.

(5) Crystallization is added 85% methanol solution for 24 h, with solid to liquid ratio was 1:8. 1.98 g raffinose can be gotten with purity as 98.5%. The recovery of raffinose in whole process was 67% basing on the mass of raffinose in defatted wheat germ. Mother liquor after crystallization could be cycled in the step of adsorption separation, so recovery was improved to 78% basing on recovery of crystallization as 100%.

Measurement Methods of Concentration of Raffinose and Sucrose

The concentration of raffinose and sucrose is measured by the following way in the above embodiment.

The analysis method of UHPLC is established by ultra performance liquid chromatograph of DIONEX D3000 and detector is corona charged aerosol detection (CAD). Chromatographic column: GRACE Prevail Carbohydrate ES (250 mm×4.6 mm, 5 μm); the liquid volume: 5 μL; mobile phase: acetonitrile-water (80:20, v/v); flow velocity: 1 mL/min; column temperature: 30° C.

Figure 2:
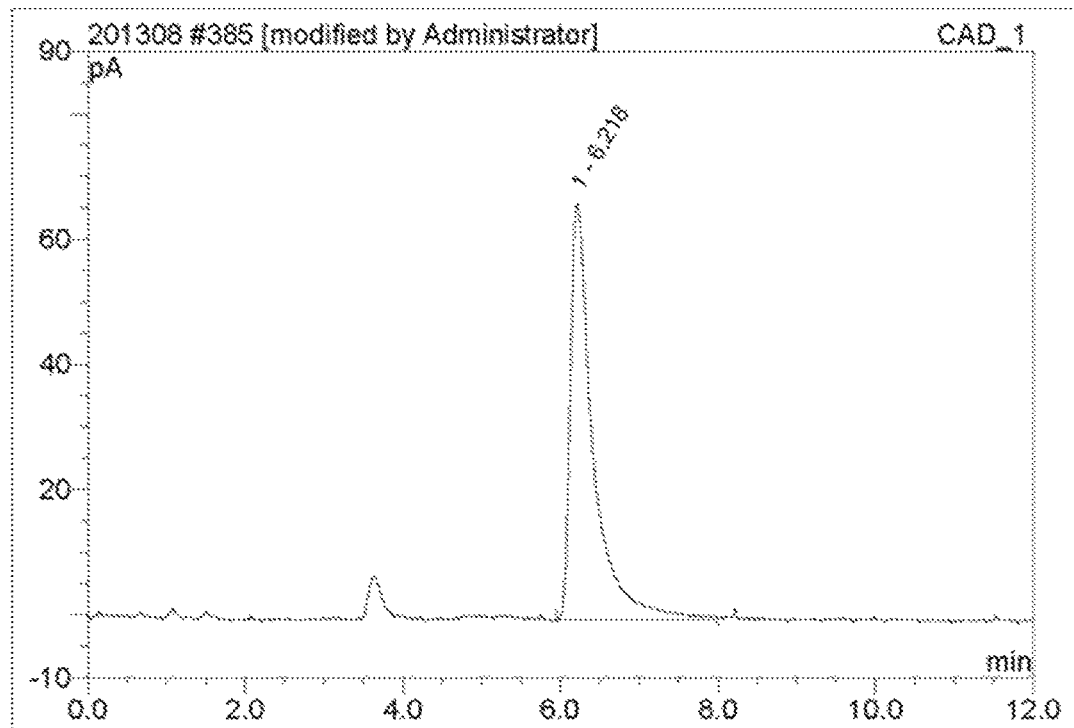
FIG. 2 HPLC chromatogram of product sucrose of the present invention
Figure 3:
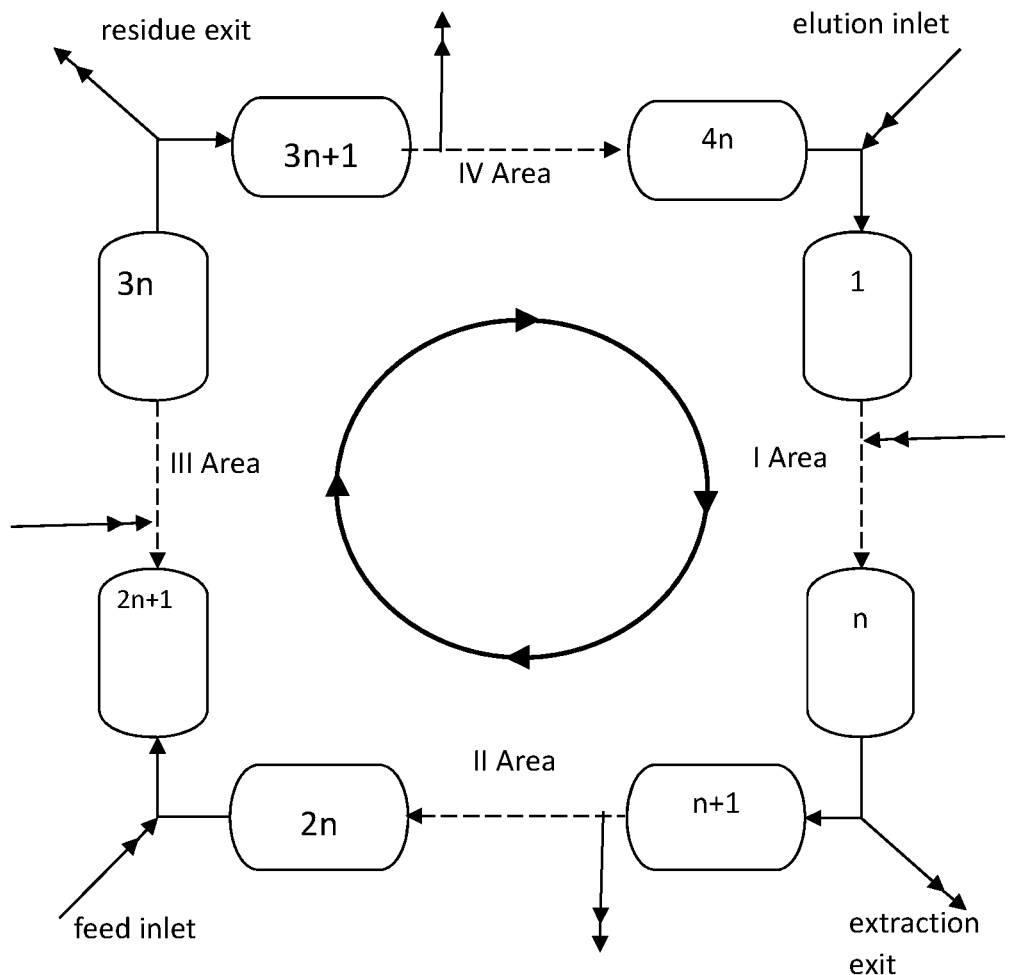
FIG. 3 Sketch of simulated moving bed equipment with four areas

The concentration range of the monosaccharides:
Raffinose: 1~6 g/L; sucrose: 1~6 g/L
The standard curve of the monosaccharides:
Raffinose: $y=2.1553*10^{-4}x_2+0.02045x$; sucrose: $y=4.01*10^{-4}x^2+0.01483x$. X—peak area, y—concentration.
Testing confirms that the retention times of raffinose and sucrose are 8.73 min (FIG. 1) and 6.22 min (FIG. 2), respectively.

The above embodiment are optimization of the present invention. To traditional technician, the improvement and polish also belong to the scope of protection of the invention, which base on the technology principle of the present invention.

The invention claimed is:

1. A process for preparing high-purity raffinose from defatted wheat germ, the method comprising the following steps:
   (1) conducting percolation extraction of the defatted wheat germ using aqueous alcohol, and collecting percolate containing raffinose, wherein the percolation extraction comprises the following sub-steps: loading percolation columns with the defatted wheat germ, then adding aqueous alcohol with a volume concentration of 60%~90%, percolating 20~60 minutes at 40~80° C. at constant pressure continuously with a flow velocity at 0.5~3 times of the volume of defatted wheat germ every hour, and collecting percolate containing raffinose at an exit until the volume of percolate being 3~5 times of the volume of the defatted wheat germ;
   (2) concentrating percolate of the step (1) to remove alcohol, dissolving solid substance in deionized water followed by filtering to remove insoluble substance, extracting the filtrate with an organic solvent and concentrating an aqueous phase to obtain a decolored solution, wherein the volume of solution after the dissolving solid substance is 15%~35% of the percolate volume;
   (3) processing the decolored solution of the step (2) through a microporous membrane of a drainage, diluting the processed solution with water to obtain a pretreatment liquid with 50~150 mg/mL solid concentration, and desalinating the pretreatment liquid by electrodialysis to obtain a desalination solution, wherein the process of the electrodialysis consists of the steps of: circulating the pretreatment liquid as concentrated phase, pure water as diluted phase and $Na_2SO_4$ polar water in an electrodialysis instrument and desalinating for 2~3 hours under constant voltage and velocity, wherein the mass concentration of $Na_2SO_4$ is 3%~8% and the volume ratio among the polar water, the pretreatment liquid and pure water is 0.25:1:(1~3);
   (4) separating the desalination solution of the step (3) with a simulated moving bed, and collecting flow material containing raffinose, followed by concentrating to obtain a supersaturated syrup, wherein the simulated moving bed equipment has four areas, containing 2~4 chromatographic column in each area, wherein the fixed-bed adsorbent of the chromatographic column is acidic (Ca) ion exchange resin or (Na) ion exchange resin, using water as an eluent; wherein the adsorbent has crosslinking degree of 2%~8% and pore size is 100~400 mesh; wherein the operation conditions of the simulated moving bed equipment: the switching time is 30~90 seconds, and velocities of flow in area I, area II, area III and area IV are 0.67~0.86, 0.44~0.70, 0.47~0.79 and 0.41~0.60 mL/min, respectively; and wherein isothermal operation is used in the simulated moving bed equipment and the column temperature is 60~80° C.; and
   (5) crystallizing the supersaturated syrup, followed by drying to obtain white crystallized raffinose, wherein the process of the crystallization comprises the steps of: dissolving the supersaturated syrup of the step (4) in alcohol at 60~90° C., and then reducing temperature to 25~40° C., inducing crystallization by adding some raffinose, filtering after crystallizing for 12~36 hours, and obtaining pure raffinose with a purity of 98% or higher after drying in a vacuum oven at 30~50° C.

2. The process for preparing high-purity raffinose from defatted wheat germ according to claim 1, wherein the volume of solution after the dissolving solid substance in the step (2) is 20%~35% of the percolate volume.

3. The process for preparing high-purity raffinose from defatted wheat germ according to claim 1, wherein the organic solvent for extracting the filtrate in the step (2) is n-butanol, iso-butanol, ethyl acetate, n-hexane or petroleum ether, and the volume of the organic solvent is 0.5~1.5 times the filtrate volume.

4. The process for preparing high-purity raffinose from defatted wheat germ according to claim 1, wherein the desalination conditions: operating voltage is 15~30 V and the liquid flow rate is 10~30 L/h.

5. The process according to claim 3, wherein the organic solvent for extracting the filtrate in the step (2) is n-butanol and the volume of n-butanol is 0.5~1.5 times the filtrate volume.

* * * * *